United States Patent [19]

West

[11] Patent Number: 5,612,372

[45] Date of Patent: Mar. 18, 1997

[54] LIQUID DISPERSANTS FOR PESTICIDES

[75] Inventor: Michael H. West, Senatobia, Miss.

[73] Assignee: IBC Manufacturing Company, Memphis, Tenn.

[21] Appl. No.: 577,020

[22] Filed: Sep. 4, 1990

[51] Int. Cl.$^6$ .......................... A01N 47/10; A01N 33/12; B01J 13/00

[52] U.S. Cl. .......................... 514/479; 252/308; 252/357; 252/389.22; 71/DIG. 1; 424/405

[58] Field of Search .................................. 252/308, 351, 252/357, 389.22; 71/DIG. 1, DIG. 4; 514/938, 941, 538, 479; 424/405

[56] References Cited

U.S. PATENT DOCUMENTS

| | | | |
|---|---|---|---|
| 3,056,722 | 10/1962 | Trademan | 514/941 X |
| 3,214,454 | 10/1965 | Blaser et al. | 252/180 X |
| 3,592,929 | 7/1971 | Nosler et al. | 424/204 |
| 4,084,952 | 4/1978 | Reynolds | 71/DIG. 1 X |
| 4,246,030 | 1/1981 | Lipinski | 252/389.22 X |
| 4,406,811 | 9/1983 | Christensen et al. | 252/389.22 X |
| 4,772,648 | 9/1988 | Demangeon et al. | 252/311.5 X |
| 4,808,215 | 2/1989 | Gill et al. | 71/DIG. 1 X |
| 4,950,685 | 8/1990 | Ward | 514/479 OR |
| 5,032,318 | 7/1991 | Bartlett | 424/405 X |
| 5,109,019 | 4/1992 | Lehmann et al. | 514/479 OR |

FOREIGN PATENT DOCUMENTS

| | | |
|---|---|---|
| 0013450 | 7/1980 | European Pat. Off. . |
| 0199383 | 10/1986 | European Pat. Off. . |
| 0314232 | 5/1989 | European Pat. Off. . |
| 0417987 | 3/1991 | European Pat. Off. . |
| 86457 | 7/1971 | German Dem. Rep. . |
| 2084128 | 4/1982 | United Kingdom . |

OTHER PUBLICATIONS

Chemical Abstracts; vol. 87 (1977) No. 87:103500p; Butcher et al.

*Hackh's Chemical Dictionary*, 4th Edition, (McGraw-Hill Book Co. New York, 1984) p. 35.

Primary Examiner—Sharon Gibson
Assistant Examiner—Daniel S. Metzmaier
Attorney, Agent, or Firm—Barnes & Thornburg

[57] ABSTRACT

Dispersant pesticide compositions which comprise a pesticide and a salt or partial salt of an alkyl substituted amine and a phosphonic acid.

10 Claims, No Drawings

LIQUID DISPERSANTS FOR PESTICIDES

This invention is concerned with compositions suitable for dispersing pesticides in water and compositions containing both a dispersant and a pesticide. In addition, it is concerned with compositions which prevent corrosion in the mild steel systems in which the water dilutions of pesticides are used or dispersed. More particularly, it pertains to compositions comprising salts or partial salts of (a) alkyl amines and/or dialkyl amines and (b) phosphonic acids, plus a water-dispersible solvent, optionally an emulsifier and a compatible pesticide. It is within the scope of the present invention to include additional components for specific purposes.

It is known to those skilled in this art that industrial biocides perform better if they are well dispersed in the water in which they are used or applied. It is also known that smaller particles of pesticides give better coverage and better prevent the entrance of pests into treated articles. It is desirable for many uses to produce a true solution of the pesticide which gives molecular size distribution.

I have found that it is possible to produce molecular dispersions in water dilutions of many water-insoluble pesticides by formulating them with the dispersant compositions of the present invention. I have also found that these molecular dispersions provide unexpectedly good levels of pesticidal activity and that the solutions are non-corrosive to mild steel.

My dispersant composition is formed by combining the following ingredients:

| | |
|---|---|
| Solvent (water dispersible) | 10–50 parts by wt |
| Commercial Liquid Phosphonic Acid | 10–40 parts by wt |
| alky or dialkyl amines | 20–60 parts by wt |
| emulsifier (optional) | 5–25 parts by wt |

Water-dispersible solvents which I have found suitable for producing compositions in accordance with this invention comprise, but are not limited to, alcohols, glycols, and glycol ethers. The water-dispersible solvent may also consist partly or totally of water itself.

Commercial liquid phosphonic acids which I have found useful for the compositions of this invention comprise, but are not limited to, the following:

Phosphonic acid, {nitrolotris (methylene)} tris

Phosphonic acid, {{{bis{2-bis(phosphonomethyl)amino}ethyl}amino}-methyle

Phosphonic acid, (1-hydroxyethylidene)bis-

Polyhexylene polyamino polymethylene phosphonic acid

Alkyl and dialkyl amines I have found useful for compositions of this invention comprise, but are not limited to, dodecyl dimethylamine, didecyl methyl amine, dodecyl amine, decyl dimethyl amine, cocodimethyl amine, N, N-dimethylcocoamine, cocoalkyldimethylamines and dicoco methyl amine.

Emulsifiers or surfactants that I have found useful for compositions of this invention comprise, but are not limited to cocodimethyl ammonium chloride, didecyl dimethyl ammonium chloride, alkyl benzyl dimethyl ammonium chlorides, and alkylphenol ethylene oxide adducts. Emulsifiers or surfactants make a better product, but since they are not absolutely essential, I consider that they are optional ingredients.

Pesticides which I have found useful when dispersed by compositions of the present invention comprise, but are not limited to, commercial compositions of polyphase, azaconazole, 2,5-dichloro 2 n-octyl-3-isothiazoline,and Tebuconazole. Useful ranges of pesticides formulated with compositions of the current invention are from about 1 to about 20 parts by weight per 100 parts by weight of the composition.

Dispersant compositions of the present invention formulated with pesticides were used for treating wood, textiles, paper, tile, brick, concrete and leather. Treating dilutions in water of from 0.1% to 10% according to the generalized formula gave control of biological growths on the treated articles which were as good or better than that offered by commercially accepted products at similar use dilutions. Compositions of the present invention with the above mentioned pesticides were also tested to determine control of algal, fungal, and bacterial slimes in water. At treating levels from 0.1% to 1%,all slimes were controlled. All of the compositions were tested at 1% in water and found to be non-corrosive to mild steel.

My dispersant composition may be combined with a pesticide in a number of different ways. For instance, the dispersant composition can be mixed with water (e.g. 100 parts of water per one part of dispersant composition) and then combined with 0.1–1.0 part of the pesticide formulation. The combination then may be further diluted with water, the degree of dilution depending upon the particular situation to be treated. This is largely a matter of routine testing that those working in this art can readily carry out in order to obtain optimum results.

The following examples illustrate some specific formulations that were prepared in accordance with my invention.

EXAMPLE I

| Ingredients | Parts by Weight |
|---|---|
| Propylene Glycol, methyl ether | 25 parts |
| Monsanto Dequest 2010 (phosphonic acid) | 15 parts |
| Ethyl ADMA 12 (amine) | 45 parts |
| GAF Igepal CO-530 (emulsifier) | 10 parts |
| Troy Polyphase AF-1 (pesticide) | 15 parts |

EXAMPLE II

| Ingredients | Parts by Weight |
|---|---|
| Ethanol, denatured | 30 parts |
| Lonza Unihib 1704 (phosphonic acid) | 10 parts |
| Ethyl DAMA 1010 (amine) | 40 parts |
| Stepan BTC 1010 (emulsifier) | 15 parts |
| Rohm and Haas Kathon 930 (pesticide) | 5 parts |

EXAMPLE III

| Ingredients | Parts by Weight |
|---|---|
| Propylene Glycol | 25 parts |
| Monsanto Dequest 2010 (phosphonic acid) | 20 parts |
| Ethyl ADMA 10 (amine) | 40 parts |
| Igelpal CO-630 (emulsifier) | 10 parts |
| Bayer AG Tebuconazole (pesticide) | 5 parts |

EXAMPLE IV

| Ingredients | Parts by Weight |
| --- | --- |
| Propylene Glycol, Methyl Ether | 15 parts |
| Albricht and Wilson Briquest 301-50-A (phosphonic acid) | 15 parts |
| Ethyl ADMA-12 (amine) | 45 parts |
| GAF Igepal CO-530 (emulsifier) | 10 parts |
| Troy Polyphase AF-1 (pesticide) | 15 parts |

EXAMPLE V

| Ingredients | Parts by Weight |
| --- | --- |
| Propylene Glycol, methyl ether | 10 parts |
| Monsanto Dequest 2010 (phosphonic acid) | 15 parts |
| N,N-dimethylcocoamine | 45 parts |
| GAF Igepal CO-530 (emulsifier) | 15 parts |
| Troy Polyphase AF-1 (pesticide) | 15 parts |

In the above examples the ingredients identified by trademarks are believed to have the following chemical constitution Bayer AG Tebuconazole is a-{2-(4-chlorophenyl)ethyl}-a-(1,1-dimethylethyl)-1H-1,2,4-triazole-1-ethanol.

Monsanto Dequest 2010 is Phosphonic acid, (1hydroxyethylidene) bis (60% in water).

GAF Igepal CO-530 is Poly (oxy-1,2-Ethandiyl), Alpha (Nonylphenyl)-Omega-Hydroxy.

Ethyl ADMA-12 is dodecyldimethylamine.

Lonza Unihib 1704 is Polyhexylene Polyamino polymethylene phosphonic acid (45% in water).

Ethyl DAMA-1010 is didecylmethylamine.

Stephan BTC-1010 is 50% didecyl dimethyl ammonium chloride in water-alcohol solvent.

Rohm-Haas Kathon 930 is 30% 4,5-Dichloro-2-n-octyl-3-isothiazoline in xylene.

Igepal CO-630 is Nonylphenoxypoly (Ethylene-oxy) Ethanol-9EO.

Ethyl ADMA 10 is decyldimethylamine.

Briquest 301-50-A is Phosphonic acid, {nitrilotiris (methylene} tris.

Troy Polyphase AF-1 is 40% 3-iodo-2-Propynyl Butyl Carbamate with 25% Hi-Flash aromatic naphtha, 15% dipropylene glycol, and 15% DMSO (Dimethyl sulfoxide).

As a further example the following pesticide formulation was prepared

| | |
| --- | --- |
| 3-Iodo-2-Propynyl Butyl Carbamate | 40% by wt |
| Hi-Flash Aromatic Naphtha | 25% by wt |
| Dipropylene Glycol | 15% by wt |
| DMSO (Dimethyl Sulfoxide) | 15% by wt | and also a dispersant composition that included

| | |
| --- | --- |
| Propylene Glycol, methyl ether | 30% by wt |
| Phosphonic Acid (1-hydroxyethylidene)bis (60% in water) | 15% by wt |
| Dodecyldimethyl amine | 45% by wt |
| Poly (oxy-1,2-Ethanediyl), Alpha-(Nonylphenyl)-Omega-Hydroxy | 10% by wt |

One part of the dispersant composition was added to 100 parts water, then one tenth of one part of the liquid pesticide formulation was added. When tested for control of sapstain on freshly cut lumber, this formulation gave better control than commercial products.

It will be apparent to those skilled in the art that many different formulation combinations must be tested to find one with optimum physical and efficacy properties. With the information given in this disclosure, the skilled chemist will be able to develop formulations of dispersant compositions and compatible pesticides with optimum physical and biological properties for a particular application.

I claim:

1. A dispersant pesticide composition which comprises
    (1) a salt or partial salt of the reaction product of
        (a) an alkyl substituted amine and
        (b) a phosphonic acid,
   and
    (2) a pesticide.

2. A dispersant pesticide composition according to claim 1 wherein said alkyl substituted amine is selected from the group consisting of dodecyldimethylamine, didecylmethylamine, dodecylamine, decyldimethylamine, N,N-dimethylcoamine, cocoalkyldimethylamine and diccocomethylamine.

3. A dispersant pesticide composition according to claim 1 wherein said amine is N,N-dimethylcocoamine.

4. A dispersant pesticide composition according to claim 1 wherein said phosphonic acid is phosphonic acid, (1-hydroxyethylidene)bis-.

5. A dispersant pesticide composition according to claim 4 wherein said amine is N,N-dimethylcocoamine.

6. A dispersant pesticide composition according to claim 2 wherein the phosphonic acid is phosphonic acid, (1-hydroxyethylidene)bis-.

7. A dispersant pesticide composition according to claim 1 wherein said amine is didecylmethylamine.

8. A dispersant pesticide composition according to claim 1 wherein said amine is dodecyldimethylamine.

9. A dispersant pesticide composition according to claim 1 wherein said amine is decyldimethylamine.

10. A dispersant pesticide composition which is formed by combining

| | |
| --- | --- |
| Propylene Glycol, methyl ether | 10 parts |
| Phosphonic acid, (1-hydroxyethyldidene)bis | 15 parts |
| N,N-dimethylcocoamine | 45 parts |
| Poly(oxy-1,2-ethandiyl), alpha(nonylphenyl)-omega-hydroxy | 15 parts |
| 40% 3-iodo-2-propynl butyl carbamate 25% hi-flush aromatic naphtha 15% dipropylene glycol, and 15% dimethyl sulfoxide | 15 parts |

* * * * *